(12) United States Patent
Le Visage et al.

(10) Patent No.: US 9,522,218 B2
(45) Date of Patent: Dec. 20, 2016

(54) METHOD FOR PREPARING POROUS SCAFFOLD FOR TISSUE ENGINEERING, CELL CULTURE AND CELL DELIVERY

(75) Inventors: Catherine Le Visage, Paris (FR); Didier Letourneur, Chatenay Malabry (FR)

(73) Assignees: INSERM (Institut National de la Santé et de la Recherche Médicale), Paris (FR); Université Paris 7—Denis Diderot, Paris (FR)

( * ) Notice: Subject to any disclaimer, the term of this patent is extended or adjusted under 35 U.S.C. 154(b) by 696 days.

(21) Appl. No.: 12/681,682

(22) PCT Filed: Oct. 10, 2008

(86) PCT No.: PCT/EP2008/063671
§ 371 (c)(1),
(2), (4) Date: Apr. 5, 2010

(87) PCT Pub. No.: WO2009/047346
PCT Pub. Date: Apr. 16, 2009

(65) Prior Publication Data
US 2010/0221303 A1    Sep. 2, 2010

(30) Foreign Application Priority Data
Oct. 11, 2007   (EP) .................... 07301452

(51) Int. Cl.
*A61L 27/20*     (2006.01)
*C08J 3/075*     (2006.01)
*C08B 37/00*     (2006.01)
*C08B 37/02*     (2006.01)
*C08B 37/04*     (2006.01)
*C08B 37/10*     (2006.01)
*C08B 37/12*     (2006.01)
*C08J 9/08*      (2006.01)
*A61L 27/52*     (2006.01)
*A61L 27/56*     (2006.01)
*A61L 27/38*     (2006.01)
*A61L 27/50*     (2006.01)
*C12N 5/00*      (2006.01)
*C08B 37/08*     (2006.01)
*C08J 9/28*      (2006.01)

(52) U.S. Cl.
CPC ........... *A61L 27/20* (2013.01); *A61L 27/3804* (2013.01); *A61L 27/3847* (2013.01); *A61L 27/3852* (2013.01); *A61L 27/507* (2013.01); *A61L 27/52* (2013.01); *A61L 27/56* (2013.01); *C08B 37/003* (2013.01); *C08B 37/0018* (2013.01); *C08B 37/0021* (2013.01); *C08B 37/0039* (2013.01); *C08B 37/0054* (2013.01); *C08B 37/0063* (2013.01); *C08B 37/0072* (2013.01); *C08B 37/0075* (2013.01); *C08B 37/0084* (2013.01); *C08J 9/08* (2013.01); *C08J 9/28* (2013.01); *C08J 9/283* (2013.01); *C12N 5/0068* (2013.01); *C08J 2201/026* (2013.01); *C08J 2201/0484* (2013.01); *C08J 2201/0504* (2013.01); *C08J 2205/022* (2013.01); *C08J 2207/10* (2013.01); *C08J 2305/00* (2013.01); *C08J 2305/02* (2013.01); *C08J 2305/04* (2013.01); *C08J 2305/08* (2013.01); *C08J 2305/10* (2013.01); *C08J 2305/12* (2013.01); *C12N 2533/70* (2013.01); *C12N 2533/72* (2013.01); *C12N 2533/74* (2013.01)

(58) Field of Classification Search
CPC .... C08J 2305/00; C08J 3/075; C08J 2205/022
See application file for complete search history.

(56) References Cited

U.S. PATENT DOCUMENTS

| 5,494,940 A * | 2/1996 | Unger ..................... B01J 20/24 521/141 |
| 5,840,777 A | 11/1998 | Eagles et al. |
| 2003/0064089 A1 | 4/2003 | Kumar |
| 2003/0163186 A1* | 8/2003 | Machy et al. ................. 623/1.1 |

(Continued)

FOREIGN PATENT DOCUMENTS

| EP | 1166987 | 1/2002 |
| WO | WO 00/61668 A1 * | 10/2000 ............... C08J 9/36 |

(Continued)

OTHER PUBLICATIONS

Zhang and Zhang (J. Biomed Mater. Res. 2002 62:378-386).*

(Continued)

*Primary Examiner* — Peter J Reddig
(74) *Attorney, Agent, or Firm* — McAndrews, Held & Malloy, Ltd.

(57) ABSTRACT

The present invention relates to a method for preparing a porous scaffold for tissue engineering. It is another object of the present invention to provide a porous scaffold obtainable by the method as above described, and its use for tissue engineering, cell culture and cell delivery. The method of the invention comprises the steps consisting of: a) preparing an alkaline aqueous solution comprising an amount of at least one polysaccharide, an amount of a cross-linking agent and an amount of a porogen agent b) transforming the solution into a hydrogel by placing said solution at a temperature from about 4° C. to about 80° C. for a sufficient time to allow the cross-linking of said amount of polysaccharide and c) submerging said hydrogel into an aqueous solution d) washing the porous scaffold obtained at step c).

5 Claims, 3 Drawing Sheets

(56) References Cited

U.S. PATENT DOCUMENTS

Figure 1:
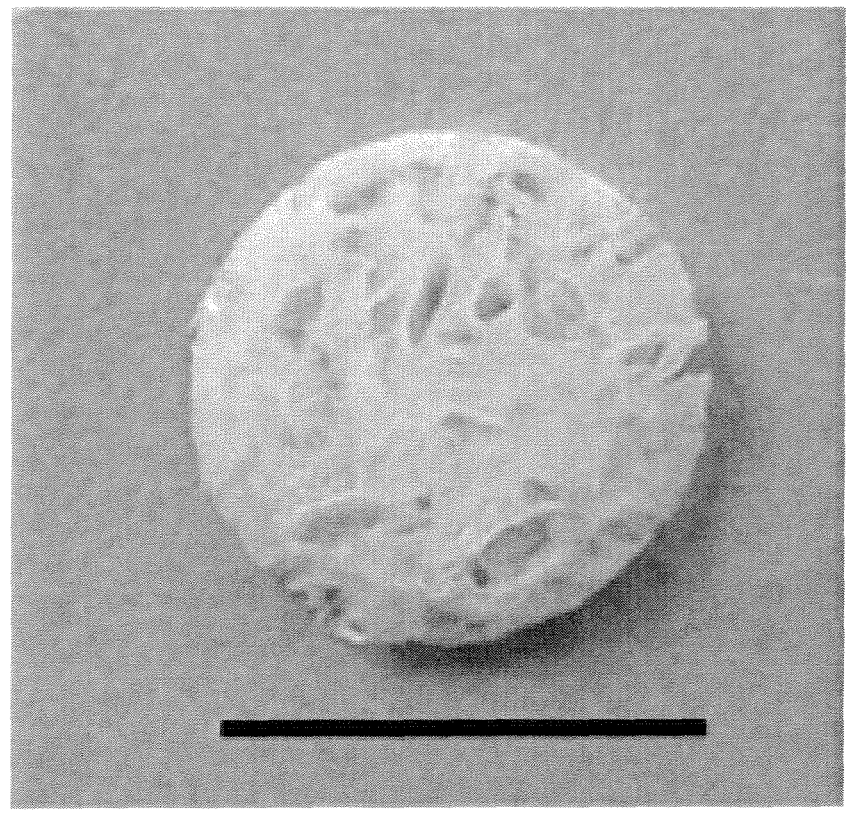

| | | | |
|---|---|---|---|
| 2003/0232895 A1* | 12/2003 | Omidian | A61K 9/0065 |
| | | | 521/99 |
| 2006/0153814 A1 | 7/2006 | Liao et al. | |
| 2009/0117656 A1* | 5/2009 | Akashi et al. | 435/397 |
| 2010/0221301 A1* | 9/2010 | Le Visage et al. | 424/422 |
| 2013/0224277 A1* | 8/2013 | Amedee et al. | 424/423 |

FOREIGN PATENT DOCUMENTS

| | | | |
|---|---|---|---|
| WO | 01/05333 | 1/2001 | |
| WO | WO 2007/061058 A1 * | 3/2007 | C08J 3/24 |

OTHER PUBLICATIONS

Barbucci et al. (J. Biomed Mater Res. Part B: Appl. Biomater. 2003 68B: 117-126).*

Sodium Bicarbonate (The Merck Index—An Encyclopedia of Chemicals, Drugs, and Biologicals (14th Edition—Version 14.9), Knovel Content, http://www.knovel.com/web/portal/basic_search/display?_EXT_KNOVEL_DISPLAY_bookid=1863, Merck & Co., Whitehouse Station, NJ, 2012).*

Thébaud et al. (J. Materials Sci.: Mater. Med. Feb. 2007 18(2): 339-345).*

Lake et al. (J. Biol. Chem.Oct. 8, 2006 281: 37,844-37,852).*

Almeida and Almeida (J. Controlled Release 2004 97:431-439).*

Sodium Bicarbonate (Cas No. 144-55-8, OECD SIDS Oct. 2002).*

International Search Report and Written Opinion in PCT/EP08/63671, dated Dec. 12, 2008.

* cited by examiner

METHOD FOR PREPARING POROUS SCAFFOLD FOR TISSUE ENGINEERING, CELL CULTURE AND CELL DELIVERY

The present application is filed pursuant to 35 U.S.C. 371 as a U.S. National Phase application of International Patent Application No. PCT/EP08/63671, which was filed Oct. 10, 2008, claiming the benefit of priority to European Patent Application No. 07301452.4, which was filed on Oct. 11, 2007. The entire text of the aforementioned applications is incorporated herein by reference in its entirety.

FIELD OF THE INVENTION

The present invention relates to a method for preparing a porous scaffold for tissue engineering. It is another object of the present invention to provide a porous scaffold obtainable by the method as above described, and its use for tissue engineering, cell culture and cell delivery

BACKGROUND OF THE INVENTION

Tissue engineering is generally defined as the creation of tissue or organ equivalents by seeding of cells onto or into a scaffold suitable for implantation. The scaffolds must be biocompatible and cells must be able to attach and proliferate on the scaffolds in order for them to form tissue or organ equivalents. These scaffolds may therefore be considered as substrates for cell growth either in vitro or in vivo.

The attributes of an ideal biocompatible scaffold would include the ability to support cell growth either in vitro or in vivo, the ability to support the growth of a wide variety of cell types or lineages, the ability to be endowed with varying degrees of flexibility or rigidity required, the ability to have varying degrees of biodegradability, the ability to be introduced into the intended site in vivo without provoking secondary damage, and the ability to serve as a vehicle or reservoir for delivery of drugs or bioactive substances to the desired site of action.

A number of different scaffold materials have been utilized, for guided tissue regeneration and/or as biocompatible surfaces. Biodegradable polymeric materials are preferred in many cases since the scaffold degrades over time and eventually the cell-scaffold structure is replaced entirely by the cells. Among the many candidates that may serve as useful scaffolds claimed to support tissue growth or regeneration, are included gels, foams, sheets, and numerous porous particulate structures of different forms and shapes.

Among the manifold natural polymers which have been disclosed to be useful for tissue engineering or culture, one can enumerate various constituents of the extracellular matrix including fibronectin, various types of collagen, and laminin, as well as keratin, fibrin and fibrinogen, hyaluronic acid, heparin sulfate, chondroitin sulfate and others.

Other common polymers that were used include poly (lactide-co-glycolide) (PLG). PLG are hydrolytically degradable polymers that are FDA approved for use in the body and mechanically strong (Thomson R C, Yaszemski M J, Powers J M, Mikos A G. Fabrication of biodegradable polymer scaffolds to engineer trabecular bone. J Biomater Sci Polym Ed. 1995; 7(1):23-38; Wong W H. Mooney D J. Synthesis and properties of biodegradable polymers used as synthetic matrices for tissue engineering. In: Atala A, Mooney D J, editors; Langer R, Vacanti J P, associate editors. Synthetic biodegradable polymer scaffolds. Boston: Birkhäuser: 1997. p. 51-82). However, they are hydrophobic and typically processed under relatively severe conditions, which make factor incorporation and entrapment of viable cells potentially a challenge.

As an alternative, a variety of hydrogels, a class of highly hydrated polymer materials (water content higher than 30% by weight), have been used as scaffold materials. They are composed of hydrophilic polymer chains, which are either synthetic or natural in origin. The structural integrity of hydrogels depends on cross-links formed between polymer chains via various chemical bonds and physical interactions.

For example, document U.S. Pat. No. 6,586,246 B1 has disclosed a method for preparing a porous hydrogel scaffold which may be used as supports for tissue engineering or culture matrices. The method of the document comprises the steps consisting of a) dissolving a biodegradable synthetic polymer in an organic solvent to prepare a polymeric solution of high viscosity b) adding a porogen agent to this solution; c) casting the polymer into a mould d) removing the organic solvent e) submerging the organic solvent-free polymer/salt gel slurry in a hot aqueous solution or acidic solution to cause the salt to effervesce at room temperature to form the porous scaffold. However, this method of preparation of a porous hydrogel involves the use of an organic solvent with a synthetic polymer which renders the method according to this invention weakly compatible with biological and therapeutic purposes.

Therefore there is still an existing need in the art to develop a method for preparing porous scaffold matrices that can be used for biological and therapeutic purposes.

SUMMARY OF THE INVENTION

Therefore, it is an object of the present invention to provide a method for preparing a porous scaffold which comprises the steps consisting of:
  a) preparing an alkaline aqueous solution comprising an amount of at least one polysaccharide, an amount of a cross-linking agent and an amount of a porogen agent.
  b) transforming the solution into a hydrogel by placing said solution at a temperature from about 4° C. to about 80° C. for a sufficient time to allow the cross-linking of said amount of polysaccharide and
  c) submerging said hydrogel into an aqueous solution
  d) washing the porous scaffold obtained at step c).

It is another object of the present invention to provide a porous scaffold obtainable by the method as above described.

It is still further an object of the present invention to provide the use of porous scaffold of the invention for tissue engineering, cell culture and cell delivery.

DETAILED DESCRIPTION OF THE INVENTION

Definitions

The term "polysaccharide", as used herein, refers to a molecule comprising two or more monosaccharide units.

The term "alkaline solution", as used herein, denotes a solution having a pH superior to 7.

The term "acidic solution", as used herein, denotes a solution having a pH inferior to 7.

The term "aqueous solution", as used herein, refers to a solution in which the solvent is water.

The term "cross-linking" refers to the linking of one polymer chain to another one with covalent bonds.

The term "porogen agent" denotes any solid agent which has the capability to form pores within a solid structure.

As used herein, a "scaffold" is defined as a semi-solid, system comprising a three-dimensional network of one or more species of polysaccharide chains. Depending on the properties of the polysaccharide (or polysaccharides) used, as well as on the nature and density of the network, such structures in equilibrium can contain various amounts of water.

The term "cross-linking agent" includes any agent able to introduce cross-link between the chains of the polysaccharides of the invention.

"Biodegradable", as used herein, refers to materials that degrade in vivo to non-toxic compounds, which can be excreted or further metabolized.

Porous Scaffolds and Method for Preparing Thereof

A first object of the invention relates to a method for preparing a porous scaffold which comprises the steps consisting of:
 a) preparing an alkaline aqueous solution comprising an amount of at least one polysaccharide, an amount of a covalent cross-linking agent and an amount of a porogen agent
 b) transforming the solution into a hydrogel by placing said solution at a temperature from about 4° C. to about 80° C. for a sufficient time to allow the cross-linking of said amount of polysaccharide and
 c) submerging said hydrogel into an aqueous solution
 d) washing the porous scaffold obtained at step c).

In the present invention, any type of polysaccharide can be used. Synthetic or natural polysaccharides may be alternatively used for the purpose of the invention. For example, suitable natural polysaccharides include, but are not limited to, dextran, agar, alginic acid, hyaluronic acid, inulin, pullulan, heparin, fucoidan, chitosan, scleroglucan, curdlan, starch, cellulose and mixtures thereof. Monosaccharides that may be used to produce the desired polysaccharide include but are not limited to ribose, glucose, mannose, galactose, fructose, sorbose, sorbitol, mannitol, iditol, dulcitol and mixtures thereof. Chemically modified polysaccharides bearing for instance acidic groups (carboxylate, sulphate, phosphate), amino groups (ethylene amine, diethylamine, diethylaminoethylamine, propylamine), hydrophobic groups (alkyl, benzyl,) can be included. Many of these compounds are available commercially from companies such as Sigma-Aldrich (St. Louis, Mich., US).

The preferred weight-average molecular weight for the polysaccharide is from about 10,000 Daltons to about 2,000,000 Daltons, more preferably from about 10,000 Daltons to about 500,000 Daltons, most preferably from about 10,000 Daltons to about 200,000 Daltons.

In one embodiment of the invention, the polysaccharide(s) used to prepare the scaffold of the invention is a neutral polysaccharide such as dextran, agar, pullulan, inulin, scleroglucan, curdlan, starch, cellulose or a mixture thereof. In a preferred embodiment, a mixture of pullulan and dextran is used to prepare the scaffold of the invention. For example, said mixture comprises 25% of dextran and 75% of pullulan.

In another embodiment of the invention, the polysaccharide(s) used to prepare the scaffold of the invention is a positively charged polysaccharide such as chitosan, DEAE-dextran and mixtures thereof.

In another embodiment of the invention, the polysaccharide(s) used to prepare the scaffold of the invention is a negatively charged polysaccharide such as alginic acid, hyaluronic acid, heparin, fucoidan and mixtures thereof.

In another embodiment of the invention, the polysaccharide(s) used to prepare the scaffold of the invention is a mixture of neutral and negatively charged polysaccharides, wherein the negatively charged polysaccharides represents 1 to 20%, preferably 5 to 10% of the mixture.

In a particular embodiment the covalent cross-linking agent is selected from the group consisting of trisodium trimetaphosphate (STMP), phosphorus oxychloride ($POCl_3$), epichlorohydrin, formaldehydes, hydrosoluble carbodiimides, glutaraldehydes or any other compound that is suitable for crosslinking a polysaccharide. In a preferred embodiment, the cross-linking agent is STMP. The concentration of the covalent cross-linking agent in the aqueous solution (w/v) is from about 1% to about 6%, more preferably from about 2% to about 6%, most preferably from about 2% to about 3%. It is preferred to use the cross-linking agent at such an amount that the weight ratio of the polysaccharide to the cross-linking agent is in the range from 20:1 to 1:1, preferably from 15:1 to 1:1 and more preferably from 10:1 to 1:1.

Many of these compounds are available commercially from companies such as Sigma-Aldrich (St. Louis, Mich., US).

The aqueous solution comprising the polysaccharide may further comprise various additives depending on the intended application. Preferably, the additive is compatible with the polysaccharide and does not interfere with the effective cross-linking of the polysaccharide(s). The amount of the additive used depends on the particular application and may be readily determined by one skilled in the art using routine experimentation.

The aqueous solution comprising the polysaccharide may optionally include at least one antimicrobial agent. Suitable antimicrobial preservatives are well known in the art. Examples of suitable antimicrobials include, but are not limited to, alkyl parabens, such as methylparaben, ethylparaben, propylparaben, and butylparaben; cresol; chlorocresol; hydroquinone; sodium benzoate; potassium benzoate; triclosan and chlorhexidine. Other examples of antibacterial agents and of anti-infectious agents that may be used are, in a nonlimiting manner, rifampicin, minocycline, chlorhexidine, silver ion agents and silver-based compositions.

The aqueous solution comprising the polysaccharide may also optionally include at least one colorant to enhance the visibility of the solution. Suitable colorants include dyes, pigments, and natural coloring agents. Examples of suitable colorants include, but are not limited to, alcian blue, fluorescein isothiocyanate (FITC) and FITCdextran.

The aqueous solution comprising the polysaccharide may also optionally include at least one surfactant. Surfactant, as used herein, refers to a compound that lowers the surface tension of water. The surfactant may be an ionic surfactant, such as sodium lauryl sulfate, or a neutral surfactant, such as polyoxyethylene ethers, polyoxyethylene esters, and polyoxyethylene sorbitan.

In a particular embodiment, the porogen agent may be an agent that can be transformed into a gas in acidic conditions, with pores being formed by the carbon dioxide molecules that leach out from the polymer. Examples of such a porogen agent include but are not limited to ammonium carbonate, ammonium bicarbonate, sodium carbonate, and sodium bicarbonate, calcium carbonate and mixtures thereof. It is preferred to use the porogen agent at such an amount that the weight ratio of the polysaccharide to the porogen agent is in the range from 6:1 to 1:1, preferably from 4:1 to 1:1, more preferably to 2:1 to 1:1. Many of these compounds are available commercially from companies such as Sigma-Aldrich (St. Louis, Mich., US). In one embodiment, the ratio of the polysaccharide to the porogen agent may be in the range from 6:1 to 0.5:1, preferably from 4:1 to 0.5:1, more preferably to 2:1 to 0.5:1. In another embodiment, while the polysaccharide is a positively charged polysaccharide, the ratio of the polysaccharide to the porogen agent may be in the range from 50:1 to 1:1, preferably from 20:1 to 1:1 and more preferably from 10:1 to 1:1.

In this particular embodiment, the aqueous solution of step c) is an acidic solution. The acid may be selected from the group consisting of citric acid, hydrochloric acid, acetic acid, formic acid, tartaric acid, salicylic acid, benzoic acid, and glutamic acid.

Alternatively, the porogen agent may be an inorganic salt that can be dissolved once the cross-linked polysaccharide scaffold is immersed in water. An example of such a porogen agent includes saturated salt solution, which would be dissolved progressively. In this particular embodiment, the aqueous solution of step c) is an aqueous solution, preferably water, and more preferably distilled water.

The concentration of the porogen agent affects the size of the pores formed in the scaffolds, so that the pore size can be under the control of the concentration of said porogen agent.

The average pore size of the scaffold is from about 1 μm to about 500 μm, preferably from about 150 μm to about 350 μm, more preferably from about 175 μm to about 300 μm. The density of the pores or porosity is from about 4% to about 75%, preferably from about 4% to about 50%.

In another embodiment, the method of the invention may comprise a further step consisting of freeze-drying the scaffold obtained at step d). Freeze-drying may be performed with any apparatus known in the art. There are essentially three categories of freeze dryers: rotary evaporators, manifold freeze dryers, and tray freeze dryers. Such apparatus are well known in the art and are commercially available such as a freeze-dryer Lyovac (GT2, STERIS Rotary vane pump, BOC EDWARDS). Basically, the vacuum of the chamber is from 0.1 mBar to about 6.5 mBar. The freeze-drying is performed for a sufficient time sufficient to remove at least 98.5% of the water, preferably at least 99% of the water, more preferably at least 99.5%.

In another embodiment, the method of the invention may comprise a further step consisting of hydrating the scaffold as prepared according to the invention. Said hydration may be performed by submerging the scaffold in an aqueous solution (e.g., de-ionized water, water filtered via reverse osmosis, a saline solution, or an aqueous solution containing a suitable active ingredient) for an amount of time sufficient to produce a scaffold having the desired water content. For example, when a scaffold comprising the maximum water content is desired, the scaffold is submerged in the aqueous solution for an amount of time sufficient to allow the scaffold to swell to its maximum size or volume. Typically, the scaffold is submerged in the aqueous solution for at least about 1 hour, preferably at least about 2 hours, and more preferably about 4 hours to about 24 hours. It is understood that the amount of time necessary to hydrate the scaffold to the desired level will depend upon several factors, such as the composition of the used polysaccharides, the size (e.g., thickness) of the scaffold, and the temperature of the aqueous solution, as well as other factors.

In a particular embodiment, the hydrated scaffold comprises 80% of water, preferably 90% of water, most preferably 95% of water.

In another particular embodiment, the aqueous solution of step a) may be poured in a mould before step b), so that the porous scaffold obtained with the method of the invention can take a desired form. Any geometrical moulds may be used according to the invention. Different sizes may be also envisaged. For example, typically, the aqueous solution may be poured in a tubular mould with a central axis so that the porous scaffold may be tubular with a desired external and internal diameter. The mould may be made of any material, but preferred material includes non sticky surfaces such as Teflon.

Alternatively, the scaffolds of the invention may be cut and shaped to take a desired size and form.

The methods of the invention can further include the step of sterilizing the scaffold using any suitable process. The scaffold can be sterilized at any suitable point, but preferably is sterilized before the scaffold is hydrated. A suitable irradiative sterilization technique is for example an irradiation with Cesium 137, 35 Gray for 10 minutes. Suitable non-irradiative sterilization techniques include, but are not limited to, UV-exposure, gas plasma or ethylene oxide methods known in the art. For example, the scaffold can be sterilized using a sterilisation system which is available from Abtox, Inc of Mundelein, Ill. under the trade mark PlazLyte, or in accordance with the gas plasma sterilization processes disclosed in U.S. Pat. No. 5,413,760 and U.S. Pat. No. 5,603,895.

The scaffold produced by the methods of the invention can be packaged in any suitable packaging material. Desirably, the packaging material maintains the sterility of the scaffold until the packaging material is breached.

In another embodiment, one or more biomolecules may be incorporated in the porous scaffold. The biomolecules may comprise, in other embodiments, drugs, hormones, antibiotics, antimicrobial substances, dyes, radioactive substances, fluorescent substances, anti-bacterial substances, chemicals or agents, including any combinations thereof. The substances may be used to enhance treatment effects, enhance visualization, indicate proper orientation, resist infection, promote healing, increase softness or any other desirable effect. In said embodiment, the scaffold of the invention, comprising one or more biomolecules as described here above, may be used as a controlled release system of an active agent.

The scaffold produced by the methods of the invention is free from growth factors and other growth stimulants. In one embodiment, the biomolecule may comprise chemotactic agents, antibiotics, steroidal or non-steroidal analgesics, antiinflammatories, immunosuppressants, anti-cancer drugs, various proteins (e.g., short chain peptides, bone morphogenic proteins, glycoprotein and lipoprotein); cell attachment mediators; biologically active ligands; integrin binding sequence; ligands; various growth and/or differentiation agents (e.g., epidermal growth factor, IGF-I, IGF-II, TGF-[beta], growth and differentiation factors, stromal derived factor SDF-1; vascular endothelial growth factors, fibroblast growth factors, platelet derived growth factors, insulin derived growth factor and transforming growth factors, parathyroid hormone, parathyroid hormone related peptide, bFGF; TGF[beta] superfamily factors; BMP-2; BMP-4; BMP-6; BMP-12; sonic hedgehog; GDF5; GDF6; GDF8; PDGF); small molecules that affect the upregulation of specific growth factors; tenascin-C; hyaluronic acid; chondroitin sulfate; fibronectin; decorin; thromboelastin; thrombin-derived peptides; heparin-binding domains; heparin; heparan sulfate; DNA fragments, DNA plasmids, Si-RNA, transfection agents or any combination thereof.

In one embodiment growth factors include heparin binding growth factor (HBGF), transforming growth factor alpha or beta (TGF.beta.), alpha fibroblastic growth factor (FGF), epidermal growth factor (TGF), vascular endothelium growth factor (VEGF), and SDF-1, some of which are also angiogenic factors. In another embodiment factors include hormones such as insulin, glucagon, and estrogen. In some embodiments it may be desirable to incorporate factors such as nerve growth factor (NGF) or muscle morphogenic factor (MMF). In one embodiment, TNF alpha/beta, or Matrix metalloproteinases (MMPs) are incorporated.

Additionally, scaffolds of the invention may optionally include anti-inflammatory agents, such as indomethacin, salicylic acid acetate, ibuprofen, sulindac, piroxicam, and naproxen; thrombogenic agents, such as thrombin, fibrinogen, homocysteine, and estramustine; and radio-opaque compounds, such as barium sulfate, gold particles and iron oxide nanoparticles (USPIOs).

Additionally, scaffolds of the invention may optionally comprise anti-thrombotic agents such as antivitamin K or aspirin, antiplatelet agents such as aspirin, thienopyridine, dipyridamole or clopidogrel (that selectively and irreversibly inhibits adenosine diphosphate (ADP)-induced platelet aggregation) or anticoagulant agent such as heparin or fucoidan. The combination of heparin (anticoagulant) and tirofiban (antiplatelet agent) has been shown to be effective in reducing both thrombus and thromboemboli and may be incorporated. Genistein, a potential isoflavone which possesses dose-dependent antiplatelet and antiproliferative properties and inhibits collagen-induced platelet aggregation responsible for primary thrombosis, may also be incorporated.

Methods for Using the Scaffolds of the Invention

Scaffolds of the invention are especially suited for tissue engineering, repair or regeneration. A difference in porosity may facilitate migration of different cell types to the appropriate regions of the scaffold. In another embodiment, a difference in porosity may facilitate development of appropriate cell-to-cell connections among the cell types comprising the scaffold, required for appropriate structuring of the developing/repairing/regenerating tissue. For example, cell processes extension may be accommodated more appropriately via the varied porosity of the scaffolding material. Therefore, the scaffold may comprise cells of any tissue.

In particular embodiment, the cells are seeded on said scaffold. In another embodiment, the scaffolds of the invention are submerged in a culture solution comprising the desired cells for an amount of time sufficient to enable penetration of the cells throughout the scaffold.

In another embodiment, scaffold of the invention is capable of supporting the viability and the growth of seeded cells in culture over long periods of time without inducing differentiation.

In another embodiment, scaffold of the invention provides an environment for unstimulated cell growth (without activation by growth stimulants)

In another embodiment, scaffold of the invention can be used to study physiological and pathological processes such as tissue growth, bone remodeling, wound healing, tumorigenesis (including migration and invasion), differentiation and angiogenesis. Scaffold allows the creation of defined and controlled environments where specific processes can be modulated and studied in a controlled manner free of endogenous factors.

In particular, scaffold of the invention can be used for 3D culture for diagnostic or toxicological dosages. In this embodiment, the scaffold of the invention would allow evaluation of the toxicity of a product directly on cells present in a 3D environment. In said embodiment, the scaffold of the invention is used for cultivating cells useful for the evaluation of the toxicity and/or pharmacology of a product, such as hepatocytes, embryonic stem cells, epithelial cells, keratinocytes, or induced pluripotent stem cells (iPS cells).

In another embodiment, scaffold of the invention is capable of supporting growth and differentiation of cell types in vitro and in vivo.

In another embodiment, the cells are stem or progenitor cells. In another embodiment the cells may include but are not limited to chondrocytes; fibrochondrocytes; osteocytes; osteoblasts; osteoclasts; synoviocytes; bone marrow cells; mesenchymal cells; epithelial cells, hepatocytes, muscle cells; stromal cells; stem cells; embryonic stem cells; precursor cells derived from adipose tissue; peripheral blood progenitor cells; stem cells isolated from adult tissue; induced pluripotent stem cells (iPS cells); genetically transformed cells; a combination of chondrocytes and other cells; a combination of osteocytes and other cells; a combination of synoviocytes and other cells; a combination of bone marrow cells and other cells; a combination of mesenchymal cells and other cells; a combination of stromal cells and other cells; a combination of stem cells and other cells; a combination of embryonic stem cells and other cells; a combination of progenitor cells isolated from adult tissue and other cells; a combination of peripheral blood progenitor cells and other cells; a combination of stem cells isolated from adult tissue and other cells; and a combination of genetically transformed cells and other cells.

In another embodiment, any of these cells for use in the scaffolds and methods of the invention, may be genetically engineered to express a desired molecule, such as for example green fluorescent protein (GFP), reporter gene (luciferase, phosphatise alkaline), heparin binding growth factor (HBGF), transforming growth factor alpha or beta (TGF.beta.), alpha fibroblastic growth factor (FGF), epidermal growth factor (TGF), vascular endothelium growth factor (VEGF) and SDF-1, some of which are also angiogenic factors. In another embodiment expressed factors include hormones such as insulin, glucagon, and estrogen. In another embodiment factors such as nerve growth factor (NGF) or muscle morphogenic factor (MMF), or in another embodiment, TNF alpha/beta are expressed.

In a particular embodiment, scaffolds of the invention are suitable to prepare vascular substitutes to replace compromised arteries as described for example, in Chaouat et al. (Chaouat M, Le Visage C, Autissier A, Chaubet F, Letourneur D. The evaluation of a small-diameter polysaccharide-based arterial graft in rats. Biomaterials. 2006 November; 27(32):5546-53. Epub 2006 Jul. 20.). Such substitutes may be prepared according to the methods of the invention by using a mould as above described. Such substitutes may then comprise a population of cells to reconstruct in vitro or in vivo a vessel. In another embodiment the cells may include but are not limited to Mesenchymal Stem Cells (MSC), Endothelial Progenitor cells (EPCs), endothelial cells, fibroblastic cells and smooth muscle cells.

In another particular embodiment, scaffolds of the invention are suitable to prepare cartilage or bone implants. In such a way, the scaffolds of the invention may be loaded with chondrocytes, osteocytes; osteoblasts; osteoclasts; vascular cells or mixtures thereof, and may be cultured in presence of differentiating agents.

The site of implantation is dependent on the diseased/injured tissue that requires treatment. For example, to treat structural defects in articular cartilage, meniscus, and bone, the cell-seeded composite scaffold will be placed at the defect site to promote repair of the damaged tissue.

In case of central nervous system (CNS) injuries, the composite scaffold can be seeded with a combination of adult neuronal stem cells, embryonic stem cells, glial cells and Sertoli cells. In the preferred embodiment, the composite scaffold can be seeded with Sertoli cells derived from transformed cell lines, xenogeneic or allogeneic sources in combination with neuronal stem cells. The Sertoli cells can be cultured with the composite scaffold for a period before addition of stem cells and subsequent implantation at the site of injury. This approach can circumvent one of the major hurdles of cell therapy for CNS applications, namely the survival of the stem cells following transplantation. A composite scaffold that entraps a large number of Sertoli cells can provide an environment that is more amenable for the survival of stem cells.

Accordingly, the porous polysaccharide scaffold, which is prepared according to the present invention, can be effectively used as a raw material for fabricating artificial tissues or organs such as artificial blood vessels, artificial bladder, artificial esophagus, artificial nerves, artificial hearts, prostatic heart valves, artificial skins, orthopedic implants, artificial muscles, artificial ligaments, artificial respiratory organs, etc. Further, the porous polysaccharide scaffold of the present invention can be prepared in the form of a hybrid tissue by blending or incorporating on or into other types of biomaterials and with functional cells derived from tissues or organs. It may have various biomedical applications, for example, to maintain cell functions, tissue regeneration, etc.

Alternatively scaffolds of the invention may be used for cell delivery. Actually, scaffolds of the invention may be used as a raw material for preparing cell delivery systems that can be administered to a subject for therapeutic or diagnostic purposes. In a particular embodiment, scaffolds of the invention may be used to prepare a patch, a biofilm or a dressing that can be loaded with cells. For example, scaffolds of the invention may used to prepare a dressing that can be applied on the skin, for reconstructing or healing the skin. Alternatively, said dressing may used to be applied on the heart of a subject for treating ischemia (myocardial infarction). In those embodiments, the cells that are entrapped in the scaffold can thus migrate into the targeted tissue or organ.

In another embodiment, scaffolds of the invention may be used for culturing cells. Cells may then be stimulated to undergo growth of differentiation or other physiological processes by the addition of appropriate growth factors. Culture medium containing one or more cytokines, growth factors, hormones or a combination thereof, may be used for maintaining cells in an undifferentiated state, or for differentiating cells into a particular pathway.

More particularly, the scaffold of the invention may be used for producing molecules of interest. Actually, scaffolds of the invention may be used to provide a biological environment for the anchorage of cells in a bioreactor, so that the cells can produced the desired molecules. The scaffolds of the invention provide mechanical and biochemical protection of the cultured cells.

The scaffolds may thus serve as a cell reservoir for producing desired molecules such as proteins, organic molecules, and nucleotides. For example, proteins of interest include but are not limited to growth factors, hormones, signal molecules, inhibitors of cell growth, and antibodies. Scaffolds of the invention are particularly interesting for producing monoclonal antibodies. Scaffolds of the invention may be also suitable to produce organic molecules such as flavours, therapeutic molecules.

In this purpose, the scaffolds of the invention may be loaded with any type of cells, including prokaryotic and eukaryotic cells. For examples, scaffolds of the invention may be load with bacteria, yeast cells, mammalian cells, insect cells, plant cells, etc. Specific examples include *E. coli*, *Kluyveromyces* or *Saccharomyces* yeasts, mammalian cell lines (e.g., Vero cells, CHO cells, 3T3 cells, COS cells, etc.) as well as primary or established mammalian cell cultures (e.g., produced from lymphoblasts, fibroblasts, embryonic cells, epithelial cells, nervous cells, adipocytes, etc.). More particularly, the invention contemplates the use of established cell lines such as hybridomas. Alternatively, the cells may be genetically engineered to express a desired molecule as described above.

The scaffold of the invention may be loaded with cells, cultured for a certain period of time then the cells can be retrived/extracted/separated from the scaffold for further use, such as therapeutic or diagnostic applications or cell analysis. Separation of the cells from the scaffold may involve the use of enzymes that could degrade the scaffold, such as pullulanase and/or the use of enzymes that could detach the cells such as collagenase, elastase, trypsin or cell-detaching solutions such as EDTA.

The invention will further be illustrated in view of the following figures and examples.

FIGURES

FIG. 1: A porous scaffold obtained as in Example 1 (Scale: 6 mm)

Figure 2:
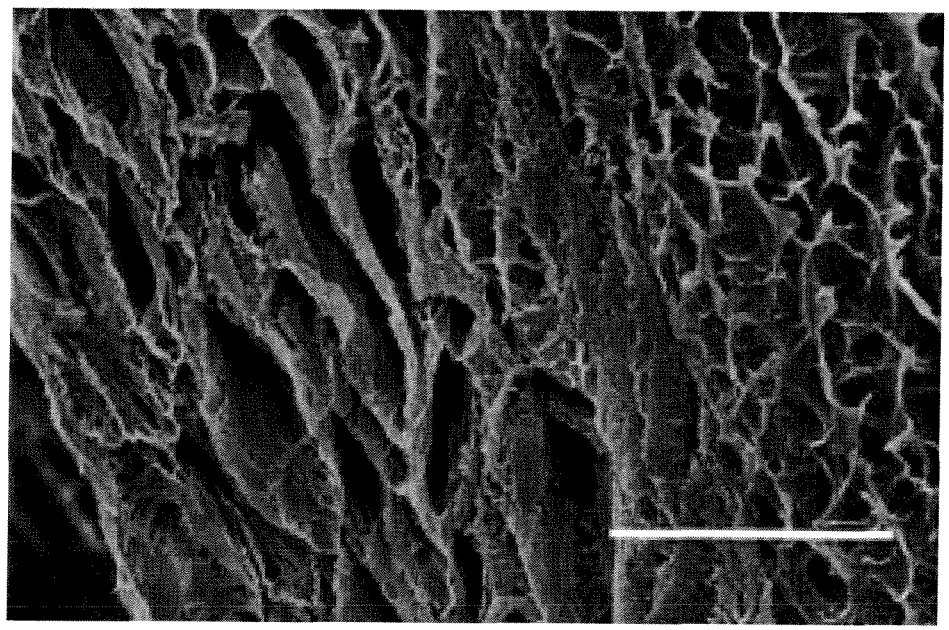

FIG. 2: A porous scaffold obtained as in Example 1: scanning Electron Microscopy analysis of the scaffold (right image, scale: 200 microns).

Figure 3:
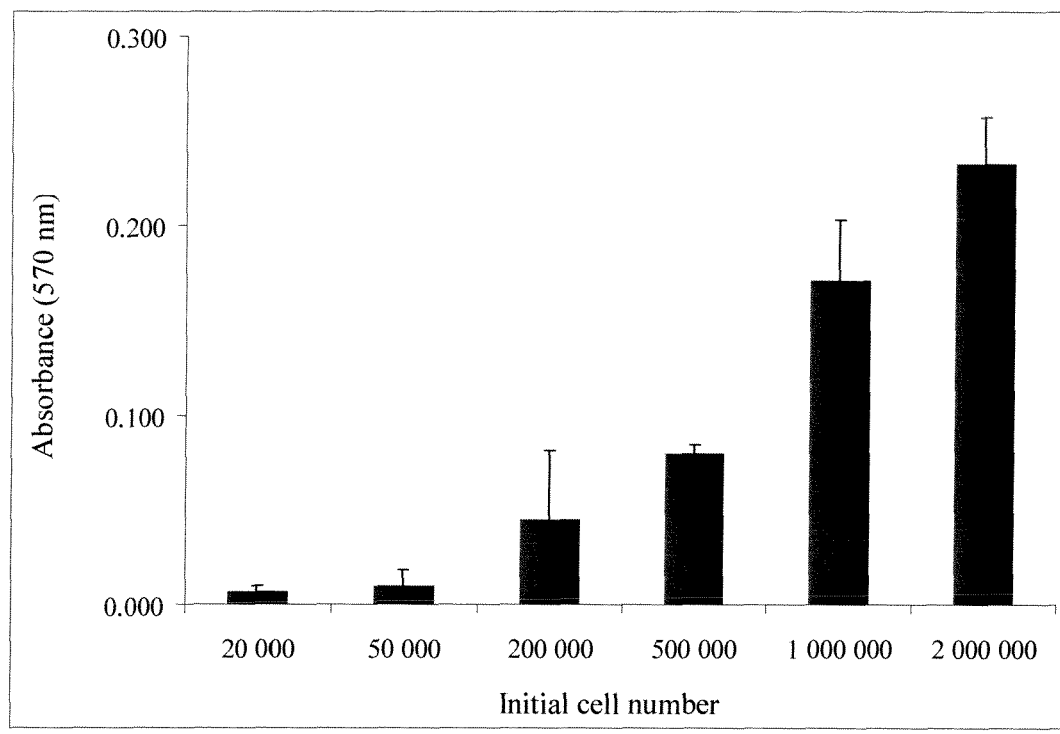

FIG. 3: Formazan absorbance (570 nm) at day 1 as a function of the initial number of cells seeded on porous scaffolds.

EXAMPLES

Example 1

Polysaccharides-Based Scaffolds Preparation

Polysaccharide-based scaffolds were prepared using using a mixture of pullulan/dextran 75:25 (pullulan, MW 200,000, Hayashibara Inc., Okayama, Japan; dextran MW 500,000, Pharmacia). A polysaccharide solution was prepared by dissolving 9 gr of pullulan and 3 gr of dextran into 40 mL of distilled water. Sodium carbonate (8 g) was then added to the polysaccharide solution and stirring was maintained until a homogeneous mixture was obtained. Chemical cross-linking of polysaccharide was carried out using the cross-linking agent trisodium trimetaphosphate STMP (Sigma, St Louis) under alkaline condition. Briefly, one milliliter of 10M sodium hydroxide was added to 10 g of the polysaccharide solution, followed by the addition of one milliliter of water containing 300 mg of STMP. The mixture was then poured into petri dishes (Nunclon®, #150288) and incubated at 50° C. for 15 min. Resulting hydrogels were immediately immersed into a large beaker containing a 20% acetic acid solution, for at least 30 minutes. Resulting scaffolds were washed extensively with phosphate buffer saline pH 7.4 then with distilled water for at least 2 days. After a freeze-drying step, porous scaffolds were stored at room temperature until use. Scanning Electron Microscopy analysis confirmed the porosity of the scaffolds (FIGS. 1 and 2).

Example 2

Types of Polysaccharides

Porous scaffolds were prepared as described in example 1, using different types and ratios of polysaccharides, while keeping the total amount of polysaccharide at a constant value. Polysaccharides were either pullulan, dextran 500, fucoidan LMW (Low Molecular Weight) and fucoidan HMW (High Molecular Weight).

| Pullulan | Dextran 500 | Fucoidan LMW | Fucoidan HMW | Solubilization | Viscosity |
|---|---|---|---|---|---|
| 100% | | | | +++ | +++ |
| | 100% | | | +/− | + |
| 50% | 50% | | | ++ | ++ |
| 75% | 25% | | | ++ | ++ |
| 75% | | 25% | | +/− | +++ |
| 75% | | | 25% | + | + |

Solubilization (+++ indicates a complete solubilization of the polysaccharides) and viscosity of the resulting polysaccharide solution (+++ indicates a very high viscosity of the solution) were visually assessed. In all cases, porous scaffolds were obtained at the end of the protocol.

Example 3

Porogen Amount

Porous scaffolds were prepared as described in example 1, while varying the amount of the porogen agent. Briefly, 2, 4 or 8 gr of sodium carbonate were added to the pullulan/dextran solution.

| Porogen agent | Solubilization | Viscosity | Porosity |
|---|---|---|---|
| 2 g | ++ | ++ | + |
| 4 g | ++ | ++ | ++ |
| 8 g | ++ | ++ | ++ |

Solubilization (++ indicates a complete solubilization of the polysaccharides), viscosity of the resulting polysaccharide solution (+++ indicates that a very high viscosity of the solution) and porosity were visually assessed. For scaffolds prepared with the lowest amount of porogen (2 g), the effervescence process was moderate, as compared to the effervescence obtained with 4 g and 8 g of porogen agent. In all cases, porous scaffolds were obtained at the end of the protocol.

Example 4

Cross-Linker Concentration

Porous scaffolds were prepared as described in example 1, while varying the amount of the cross-linking agent from 200 mg to 500 mg.

| Cross-linking agent | Solubilization | Viscosity | Porosity |
|---|---|---|---|
| 200 mg | ++ | ++ | ++ |
| 300 mg | ++ | ++ | ++ |
| 400 mg | ++ | +++ | ++ |
| 500 mg | ++ | +++ | + |

Solubilization (+++ indicates a complete solubilization of the polysaccharides), viscosity of the resulting polysaccharide solution (+++ indicates that a very high viscosity of the solution) and porosity were visually assessed. In all cases, porous scaffolds were obtained at the end of the protocol.

Example 5

Cell Loading into the Porous Scaffolds

Human bone marrow Mesenchymal Stem Cells (hMSC) were cultured on scaffolds prepared as in Example 1. A circular punch was used to cut 6 mm diameter and 1 mm thickness round-shaped porous scaffolds. Culture medium consisted of low glucose DMEM (Gibco, Life Technology, New York) with 10% fetal bovine serum and 1% penicillin/streptomycin (Sigma). After cell trypsinization, rehydration of the dried scaffold was performed with 20 μL of cell suspension ($10^6$ cells/scaffold). Samples were then maintained in 1 mL of culture medium for up to 1 week. Non-seeded porous scaffolds incubated in culture medium were used as controls.

A metabolic assay (MTT, 3-(4,5-dimethyldiazol-2-yl)-2,5-diphenyl tetrazolium bromide, Sigma) was performed to assess the cell viability. Briefly, a 5 mg/mL stock solution of MU (Sigma) was mixed 1:10 with DMEM. Scaffolds were incubated for 3 h at 37 C with 1 mL of the reagent solution. After washing the scaffolds with PBS, the formazan crystals were solubilized in 0.3 mL of Isopropranol/HCl 0.04M. Absorbance was recorded at 590 nm with a microplate reader (Multiskan, Thermo Electron Corporation, Waltham, Mass.). Absorbance at day 1 was directly proportional to the initial number of cells seeded in the scaffolds (FIG. 3).

Similar experiments were successfully carried out with other cell types such as primary vascular smooth muscle cells and endothelial cells from animal and human origin.

Example 6

Confocal Analysis of Cell Behavior within the Porous Scaffolds

Fluorescent scaffolds were prepared as in example 1, by adding a small amount (5 mg) of FITC-dextran to the polysaccharide solution. Fluorescent scaffolds were seeded as in Example 5, with hMSC labeled with a fluorescent marker (PKH26, SIGMA P9691) according to the manufacturer's instructions). Confocal imaging confirmed the porous structure of the scaffold.

Example 7

Cell Viability by Live and Dead Assay

Confocal imaging was used to assess the cell viability with a live/dead assay (Calbiochem, San Diego, Calif.), based on the use of two fluorescent probes that measure the cell membrane permeability: a cell-permeable green fluorescent dye to stain live cells (calcein AM) and a cell nonpermeable red fluorescent dye (propidium iodide) to stain dead cells. At day 7, most of the cells were live cells, with only few dead cells found within the scaffolds.

Example 8

Influence of the Porogen Agent on Scaffold Porosity

Porous scaffolds were prepared as described in example 1, while varying the amount and the nature of the porogen agent. For confocal analysis of fluorescent porous scaffolds, 5 mg of FITC-dextran were added to the polysaccharide solution. Optical sections were acquired using a Zeiss LSM 510 confocal microscope (Carl Zeiss, Oberkochen, Germany), equipped with a 10× Plan-NeoFluar objective lens (numerical aperture of 0.3) (Carl Zeiss). FITC-dextran was excited at 488 nm with an argon laser and its fluorescent emission was selected by a 505-530 nm bandpass filter. Pore size was assessed with ImageJ® software. Void volume was calculated with a statistics/volume measurement module from Amira® software and results are expressed as a percentage of the scaffold volume.

| Polysaccharides | Porogen agent | Mean diameter (µm) | Void volume (%) |
|---|---|---|---|
| Pullulan (9 g) + dextran 500 (3 g) | Sodium Carbonate (8 g) | 195 | 37% |
| Pullulan (9 g) + dextran 500 (3 g) | Sodium Carbonate (8 g) + Sodium Chloride (2 g) | 207 | 71% |
| Pullulan (9 g) + dextran 500 (3 g) | Sodium Carbonate (8 g) + Sodium Chloride (8 g) | 272 | 59% |

Example 9

Positively Charged Polysaccharide

Positively charged porous scaffolds were prepared using using DEAE-Dextran as the only polysaccharide. Briefly, DEAE-dextran solution was prepared by dissolving 1 g of DEAE-dextran (Fluka reference #30461) into 1.5 mL of distilled water. Sodium carbonate (100 mg) was then added to the polysaccharide solution and stirring was maintained until a homogeneous mixture was obtained. Chemical cross-linking of polysaccharide was carried out using the cross-linking agent trisodium trimetaphosphate STMP (Sigma, St Louis) under alkaline condition.

Briefly, 150 µL of 10M sodium hydroxide was added to the polysaccharide solution, followed by the addition of 150 µL of water containing 45 mg of STMP. The mixture was then poured into petri dishes (Nunclon®, #150288) and incubated at 50° C. for 15 min. Resulting hydrogels were immediately immersed into a large beaker containing a 20% acetic acid solution, for at least 30 minutes. Resulting scaffolds were washed extensively with phosphate buffer saline pH 7.4 then with distilled water for at least 2 days. After a freeze-drying step, porous scaffolds were obtained and stored at room temperature until use.

Example 10

Negatively Charged Polysaccharide

Negatively charged porous scaffolds were prepared by adding fucoidan (Sigma reference #F5631) to a pullulan/dextran mixture. Briefly, a polysaccharide solution was prepared by dissolving 9 g of pullulan and 3 g of dextran into 40 mL of distilled water, then adding 1.2 g of fucoidan into the polysaccharide solution. Sodium carbonate (8 g) was then added to the polysaccharide solution and the cross-linking process was carried out as described in Example 1 to obtain a 3D scaffold that contains a negatively charged polysaccharide.

Example 11

Differentiation of Human Mesenchymal Stem Cells into Chondrocyte-Like Cells in 3D Scaffolds Human bone marrow Mesenchymal Stem Cells (hMSC) were cultured on scaffolds prepared as in Example 1 in serum-free chondrogenic medium. Chondrogenic medium consisted of DMEM supplemented with 10 ng/ml TGF-β3 (Oncogene, Cambridge, Mass.), 100 nM dexamethasone (Sigma, St Louis, Mo.), 170 µM ascorbic acid 2-phosphate (Sigma, St Louis, Mo.) and 5 mL of ITS-plus (Collaborative Biomedical Products, Bedford, Mass.). After 3 weeks of culture, seeded scaffolds were fixed in formaldehyde 10% then cryosectioned. Frozen sections were stained with either 0.05% (w/v) toluidine blue or with 0.1% safranin O solution. A strong positive staining for extracellular matrix synthesis was observed, indicating MSC differentiation into cartilage cells.

Example 12

3D Culture of Hepatocytes

HepG2 cells, human hepatocellular carcinoma cells, were cultured in low glucose DMEM (Gibco, Life Technology, New York, USA) with 10% fetal bovine serum and 1% penicillin/streptomycin (Sigma) on scaffolds prepared as in Example 1. A circular punch was used to cut 6 mm diameter and 1 mm thickness round-shaped porous scaffolds.

After cell trypsinization, rehydration of the dried scaffold was performed with 20 µL of cell suspension (85,000 cells/scaffold). Samples were then maintained in 1 mL of culture medium for up to 1 week. Non-seeded porous scaffolds incubated in culture medium were used as controls. Hepatocyte spheroids formation was observed after 4 days of culture. Cell viability in spheroids was assayed using Calcein AM (Calbiochem, San Diego Calif., USA) which is a polyanionic dye hydrolyzed by live cells thus producing an intense uniform green fluorescence (wavelength 485-535 nm), according to the manufacturer's instructions. The seeded scaffolds contained living hepatocytes suitable for pharmaco-toxicological assays.

The invention claimed is:

1. A method for preparing a porous scaffold which consists of the following steps:
   a) preparing an alkaline aqueous solution comprising an amount of at least one polysaccharide selected from the group consisting of dextran, agar, pullulan, inulin, heparin, fucoidan, and mixtures thereof; an amount of a covalent cross-linking agent selected from the group consisting of trisodium trimetaphosphate (STMP), phosphorus oxychloride ($POCl_3$), epichlorohydrin, formaldehydes, and glutaraldehydes; and an amount of a porogen agent selected from the group consisting of ammonium carbonate, ammonium bicarbonate, calcium carbonate, sodium carbonate, and sodium bicarbonate and mixtures thereof;
   b) transforming the solution into a hydrogel by placing said solution at a temperature from about 4° C. to about 80° C. for a sufficient time to allow the cross-linking of said amount of polysaccharide;
c) submerging said hydrogel into an aqueous acidic solution to form pores; and
d) washing the porous scaffold obtained at step c), wherein
the porous scaffold is a hydrogel;
the porogen agent is dissolved in step a);
the weight ratio of the polysaccharide to the porogen agent is in the range from 6:1 to 1:1; and
wherein the alkaline aqueous solution in a) does not include a surfactant.

2. The method according to claim 1 wherein the weight ratio of the polysaccharide to the cross-linking agent is in the range from 15:1 to 1:1.

3. The method according to claim 1 wherein the solution of step a) is poured in a mould before step b).

4. The method according to claim 1 wherein said scaffold is shaped.

5. The method according to claim 1 wherein the porogen agent is selected from the group consisting of ammonium carbonate, calcium carbonate, sodium carbonate, sodium bicarbonate, and mixtures thereof.

* * * * *